(12) United States Patent
Benco et al.

(10) Patent No.: US 6,660,526 B2
(45) Date of Patent: Dec. 9, 2003

(54) POTASSIUM FLUOROIONOPHORE

(75) Inventors: John S. Benco, Medfield, MA (US); W. Grant McGimpsey, Worcester, MA (US); Hubert Nienaber, Worcester, MA (US)

(73) Assignees: Bayer Corporation, E. Walpole, MA (US); Worcester Polytechnic Institute, Worcester, MA (US)

( * ) Notice: Subject to any disclaimer, the term of this patent is extended or adjusted under 35 U.S.C. 154(b) by 126 days.

(21) Appl. No.: 10/029,542

(22) Filed: Dec. 21, 2001

(65) Prior Publication Data

US 2003/0119195 A1 Jun. 26, 2003

(51) Int. Cl.$^7$ ............................................... G01N 21/76
(52) U.S. Cl. ........................ 436/79; 436/172; 422/82.08
(58) Field of Search .......................... 436/73, 74, 79, 436/172, 800; 422/82.07, 82.08; 549/346, 347

(56) References Cited

U.S. PATENT DOCUMENTS

| | | |
|---|---|---|
| 5,308,468 A | 5/1994 | Katoh et al. ................ 204/419 |
| 5,439,828 A | 8/1995 | Masilamani et al. |
| 5,641,684 A | 6/1997 | Moore et al. |
| 6,143,570 A | 11/2000 | Alder et al. |
| 6,294,390 B1 | 9/2001 | Barnard et al. ............. 436/172 |

FOREIGN PATENT DOCUMENTS

WO    WO 97/39337 A1    10/1997

OTHER PUBLICATIONS

Kim, J.S. et al "Molecular Taekwando. 2. A New Calix[4] azacrown Bearing two Different Binding Sites as a New Fluorescent Ionophore" J. Org. Chem. Vol 68, 597–600 (2003).*
Bühlmann P et al., *Chem Rev.* 98: 1593–1687 (Jun. 4, 1998).
Casnati A et al., *Chem. Eur. J.* 2: 436–445 (1996).
Casnati A et al., *J. Am. Chem. Soc.* 117: 2767–2777 (1995).
de Silva A et al., *Chem. Rev.* 97: 1515–1556 (1997).
Harrowfield J, *Lecture Notes Biological Inorganic Chemistry, Third Year Chemistry*, Topic BI, 3.2.1.3 Ionophore Selectivity (The University of Western Australia Department of Chemistry, 2001).
Ji H et al., *Photochem. Photobiol.* 70: 882–886 (1999).
Kim JS et al, *Microchem. J.* 58: 225–235 (1998).
Kim JS et al., *J. Org. Chem.* 65: 2386–2392 (2000).

* cited by examiner

*Primary Examiner*—Jeffrey Snay
(74) *Attorney, Agent, or Firm*—John T. Prince; McDermott, Will & Emery

(57) ABSTRACT

A fluoroionophore for the fluorescent detection of potassium ions.

28 Claims, 2 Drawing Sheets

POTASSIUM FLUOROIONOPHORE

FIELD OF THE INVENTION

The invention relates generally to the detection of ions by ion selective compounds. More particularly, the invention relates to the detection of potassium ions.

BACKGROUND OF THE INVENTION

Ion selective electrodes are widely used in analytical chemistry to measure the concentration of specific ionic substances in fluids ranging from drinking water to biological fluids, such as whole blood, plasma, serum and urine. Typical ions that have been measured using ion selective electrodes include sodium, calcium, iodide, magnesium, potassium, chloride, and lithium.

Valinomycin is used as an ionophore in the most widely used potassium selective membrane electrodes.

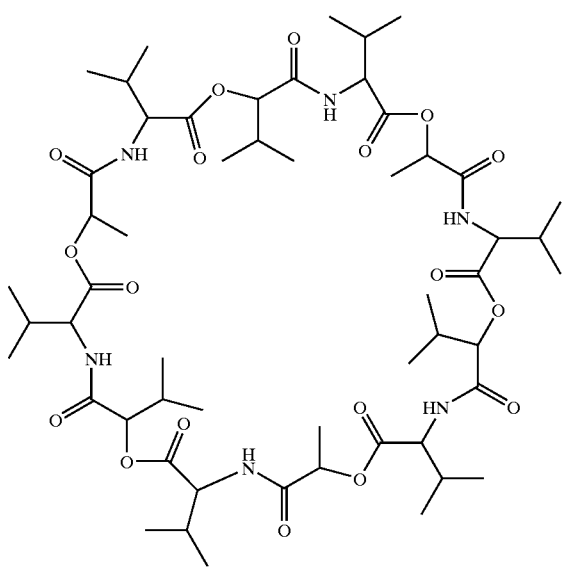

The antibiotic valinomycin is possibly the best-known neutral carrier for potassium ion in nature. The presence of valinomycin enables the organic membrane to exhibit a voltage (EMF) that is highly dependent on the potassium activity in the sample.

However, there is a need in the art for ionophores suitable for the fluorescent detection of potassium ions.

SUMMARY OF THE INVENTION

The invention provides a fluoroionophore based upon the covalent linkage of a fluorophore to a crown-5 calix[4]arene ionophore. The compound (1) has the following general structure:

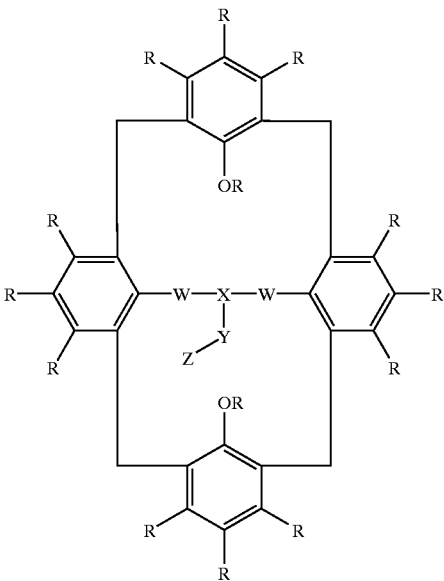

where (a) R is hydrogen, a saturated or unsaturated alkyl or aryl group, an ether, a carboxylic acid or ester group, or an alkyl or aryl group containing nitrogen or sulfur, independently or in combination; (b) W is —O(CH$_2$)$_2$O(CH$_2$)$_2$—; (c) X is nitrogen, substituted or unsubstituted aryl, with or without heteroatoms, such as nitrogen, sulfur, oxygen, or saturated and unsaturated alkyl, (d) Y is saturated or unsaturated alkyl or aryl, ether, carboxylic containing, nitrogen or sulfur independently or in combination and (e) Z is an unsubstituted or substituted aryl group or groups (a fluorophore), such that the presence of Z in the compound allows for a negative, thermo-neutral or slightly positive free energy value to be obtained from the Rehm-Weller equation for the compound.

In a particular embodiment, the molecule has the following structure (2):

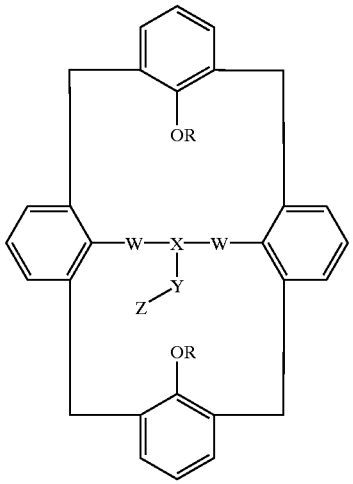

where (a) R is propyl; (b) W is —O(CH$_2$)$_2$O(CH$_2$)$_2$—; (c) X is nitrogen, (d)Y is —CH$_2$— and (e) Z, the fluorophore, is anthracene.

The invention also provides a method of synthesizing the fluoroionophore of the invention. The invention further provides an optode containing the fluoroionophore of the invention.

DETAILED DESCRIPTION OF THE INVENTION

Figure 1:
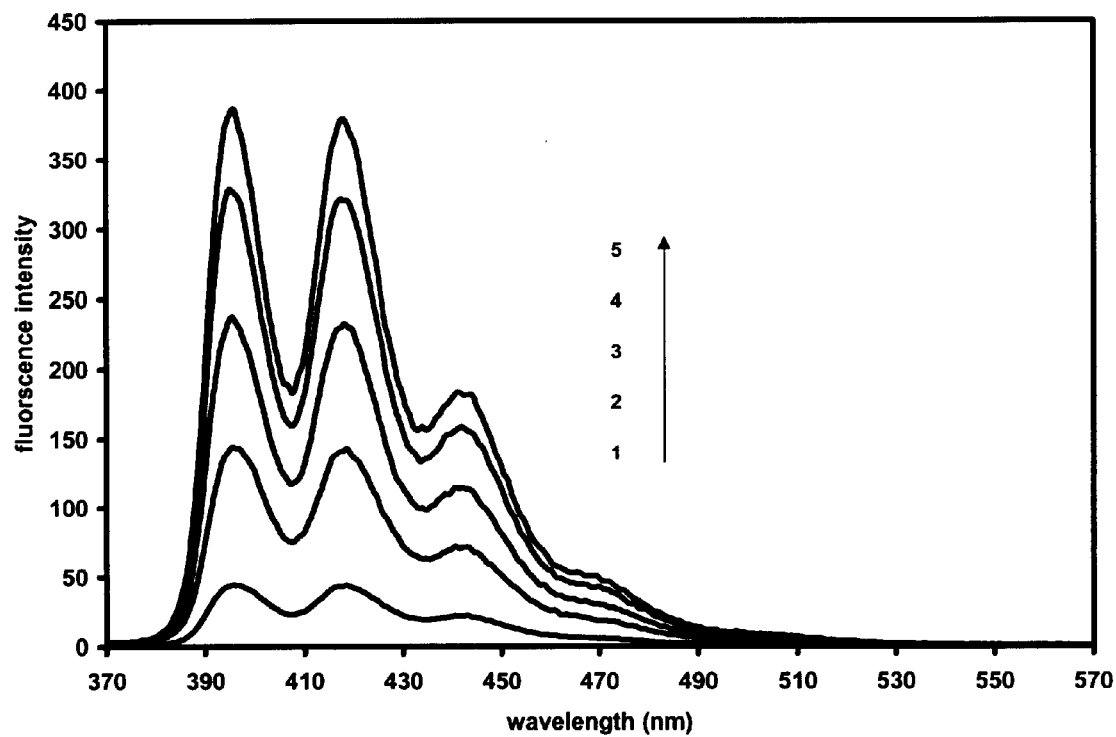
FIG. 1 shows the fluorescence emission spectrum of the title compound as a function of potassium concentration, where 1, 2, 3, 4, and 5 are 0, 0.5, 1, 1.5, and 2 μM final potassium concentrations, respectively.

The compound of the invention includes three components, namely (a) a fluorophore or other chromophore, (b) a host-guest site (ionophore) and (c) a spacer module. The interaction of the potassium ion with the ionophore moderates an internal electron transfer that alters the fluorescence intensity (quantum yield) of the fluorophore. The use of fluorescence (in contrast to absorbance) provides a means to reduce the sensor size dramatically while retaining the same signal-to-noise ratio.

Regarding the ionophore, ether crown-5 and aza crown-5 calix[4]arenes are known to be excellent ionophores for the selective complexation and determination of potassium ions in solution. An example of such an ionophore has been reported by Casnati A et al., "1,3-Alternate Calix[4] arenecrown-5 Conformers: New Synthetic Ionophores with Better K$^+$/Na$^+$ Selectivity than Valinomycin", *Chem. Eur. J.* 2: 436–445 (1996).

By using an aza crown calixarene, a convenient attachment site for a fluorophore (or other chromophore) is available via the secondary amine. Covalent attachment can be accomplished by any one of several methods well known to those of skill in the art.

However, ionophores having other structures can also be used as part of the fluoroionophore of the invention. For the compound having the structure:

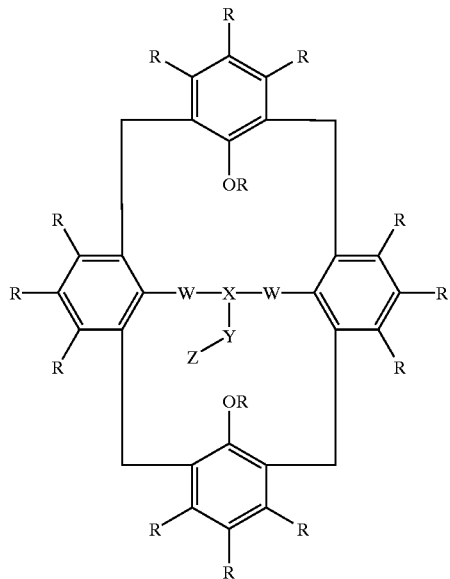

R can be, independently or in combination, a hydrogen, an alkyl, alkenyl, alkynyl, alkoxy, ether, acyl, carboxylic acid, carboxylic ester, unsubstituted aryl substituted aryl, aryloxy, heteroaryl, or heteroaryloxy group, where the heteroatom in the is selected from nitrogen and sulfur. X can be, independently or in combination, a nitrogen, or saturated alkyl, unsaturated alkyl, unsubstituted aryl, or substituted aryl group, where the aryl group may contain a heteroatom selected from the group consisting of nitrogen, sulfur and oxygen. Y can be, independently or in combination, a saturated alkyl, unsaturated alkyl, unsubstituted aryl, or substituted aryl group, or an ether, carboxylic acid, or carboxylic ester group, or a secondary amine or a sulfur atom. Other suitable groups and further descriptions of the groups described here can be determined by one of skill in the art by reference to an organic chemistry textbook (for example, Bruice P Y, *Organic Chemistry, Third Edition* (Prentice-Hall, 2001) or Wade L W, *Organic Chemistry, Fourth Edition,* (Prentice-Hall, 1999)).

Suitable fluorophores or chromophores can be any fluorophores or chromophores that satisfy the needed application. Particularly good fluorophores are ones that allow for a negative, thermo-neutral or slightly positive free energy value to be obtained from the Rehm-Weller equation (Rehm D & Weller A, *Isr. J. Chem* 8: 259–271 (1970)).

$$\Delta G^\circ = E_{ox}^\circ(\text{donor}) - E_{red}^\circ(\text{acceptor}) - E_{0,0} + C$$

where $E_{ox}^\circ$(donor) is the oxidation potential of the donor group (i.e. nitrogen), $E_{red}^\circ$(acceptor) is the reduction potential of the acceptor group (i.e. fluorophore), $E_{0,0}$ is the singlet state energy of the fluorophore and C is a Coulombic term relating to the energy of separated ions and which can be neglected in aqueous solutions (Weller A Z, *Phys. Chem. Neu. Folg.* 133: 93 (1982)).

An acceptable "slightly positive free energy value" can be in the range of 0–10 kcal/mol. A preferred free energy value can be determined by one of skill in the art depending on electron donor/fluorophore pair chosen and the temperature.

Fluorophores can be obtain from commercial sources, for example from Molecular Probes, Inc., (Eugene, Oreg., USA) or Amersham Pharmacia Biotech (Buckinghamshire, England, UK).

Signal transduction in the fluoroionophore of the invention is modulated by the photoinduced electron transfer (PET) mechanism, well known to those of skill in the art. Specifically, ion complexation within the aza-crown-5 calix [4]arene binding site suppresses electron transfer to the excited fluorophore and thereby increases the fluorescence intensity. The increase of fluorescence can be related linearly to the measured ion concentration or activity. An extensive review of the subject matter has been given by de Silva A et al., "Signaling Recognition Events with Fluorescent Sensors and Switches", *Chem. Rev.* 97: 1515–1556 (1997).

A fluoroionophore different from the compound of the invention has been described by Ji H et al., "Optical Sensing of Cesium Using 1,3-Aternate Calix[4]-mono- and Di(anthrylmethyl)aza-crown-6", *Photochem. Photobio.* 70: 882–886 (1999), which operates on the same signal transduction principle as the fluoroionophore of the invention, but which uses a much larger aza-crown cavity suitable for the detection of cesium and not potassium. In addition, the compound of the invention advantageously uses fewer fluorophore linkage sites, for easier synthesis.

Another fluoroionophore different from the compound of the invention has been described by Kim J S et al., "Synthesis and Metal Ion Complexation Studies of Proton-Ionizable Calix[4]azacrown Ethers in the 1,3-Alternate Conformation", *J. Org. Chem.* 65: 2386–2392 (2000), which uses a similar aza-crown calix[4]arene ionophore structure as the ionophore of the invention, but which is covalently linked to a proton-ionizable chromophore. As such, signal transduction is monitored by the less sensitive technique of absorption as compared to fluorescence. Moreover, the molecule is pH sensitive and thus restricts its use to samples where the proton concentration is controlled. By contrast, signal transduction in the compound of the invention can advantageously be measured by fluorescence over a range of proton concentrations.

The compound of the invention can be used directly to measure intracellular cytosolic potassium ion activity or levels of potassium in fluid samples, for example biological samples. By "biological sample" is meant any fluid of biological origin, including fluids of biological origin which have been chemically or physically treated, diluted, or concentrated prior to analysis. Examples of biological samples include serum, urine, plasma, whole blood, cerebrospinal fluid, amniotic fluid, saliva and tears.

The fluoroionophore of the invention can also be introduced into cells of organisms, using methods known to those of skill in the art (see, *Handbook of Fluorescent Probes and Research Products, Eighth Edition* (Molecular Probes, Eugene Oreg., 2001)). The potassium-dependent emission can be measured by a commercially available intracellular imaging device (for example, from Image Solutions, Standish, Wigan, UK), containing, for example, an epifluorescence/phase contrast microscope, microphotometer assembly, and image processing computer.

The invention also provides a potassium sensor, referred to as an "optode" or "optrode", which include the fluoroionophore of the invention and a transparent support material in which the ionophore is situated (see, for comparison, Bühlmann P et al., *Chem Rev.* 98: 1593–1687 (1998)). A material is "transparent" for the purposes of this invention if the material is substantially transparent to the wavelength of light that excites the fluoroionophore and the wavelength of light that is emitted from the fluoroionophore, where the excitation wavelength and the emission wavelength are the wavelengths relevant to the actual measurement. For example, the emission from the fluoroionophore can be measured by spectrofluorimetry, a technique that is well known to those of skill in the art. Spectrofluorimeters are commercially available, for example from Perkin Elmer (Shelton, Conn., USA). The excitation and emission spectra of the fluoroionophore can be estimated by one of skill in the art based upon published excitation and emission spectra for the fluorophore and for similar fluorophores.

Under the appropriate conditions, the use of optode of the invention advantageously provides continuous measurement of potassium ion activity in situ and in real-time.

In one embodiment, the fluoroionophore of the invention is retained in a plasticized poly(vinyl chloride) (PVC) film as the support material. In a further embodiment, the film is placed on the end of an optically conductive fiber (an optic fiber bundle). The optic fiber bundle can be connected directly to a spectrofluorimeter for ease of measurement. Commercially obtainable optic fiber bundles may be used.

In other embodiments, the support material is a material selected from PVC, Nafion and sol-gel materials such as silicate or mixtures such as polyvinylformal-silica (see, Flamini & Panusa, *Sens. Actuators,* B42: 39 (1997)).

In one embodiment, the compound of the invention is covalently immobilized to the support material through attachment to the ionophore through the R groups or to the fluorophore (see, U.S. Pat. No. 6,294,390).

The details of one or more embodiments of the invention are set forth in the accompanying description. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

Synthesis of the Compound of the Invention

Synthesis of Compound 2: Mass spectra were performed by SYNPEP Corporation, Dublin, Calif. Melting points are measured in a capillary melting point apparatus and are not corrected. $^1$H- and $^{13}$C-NMR spectra were recorded with a Bruker Avance 400 in $CDCl_3$. All solvents and reagents were used as supplied unless stated otherwise. Calix[4]arene was purchased from Acros Organics (a Fisher Scientific Company).

Preparation of 25,27-bis(1-propyloxy)calix[4]arene: The preparation of dipropyl-calix[4]arene followed the method described in Kim J S et al., *Microchem. J.* 58: 225–235 (1998). In a 250 ml round bottom flask, 5.08 g calix[4]arene (11.9 mmol), 4.87 g 1-Iodopropane (28.6 mmol) and 3.95 g (28.6 mmol) $K_2CO_3$ were suspended in 150 ml dry acetonitrile and boiled under reflux for 24 hours. The solvent was removed in vacuo and 50 ml 2N HCl and 50 ml $CH_2Cl_2$ were added and the phases were separated. The aqueous phase was extracted two times with 30 ml $CH_2Cl_2$, the organic phases were combined dried with $Na_2SO_4$ and the solvent removed in vacuo. The crude product was recrystallized from methanol/$CH_2Cl_2$ (5:1) and gave 4.37 g (72%) of 25,27-bis(1-propyloxy)calix[4]arene as white crystals.

The $^1$H NMR spectrum corresponds to the published data by Casnati A et al., *J. Am. Chem. Soc.,* 117, 2767–2777 (1995). $^1$H NMR ($CDCl_3$) δ1.32 (t, J=7.3 Hz, 6H, $OCH_2CH_2CH_3$), 2.08 (m, 4H, $OCH_2CH_2CH_3$), 3.40 (d, J=12.9 Hz, 4H, Ar—$CH_2$—Ar), 3.98 (t, J=6.2 Hz, 4H, $OCH_2CH_2CH_3$), 4.35 (d, J=12.9 Hz, 4H, Ar—$CH_2$—Ar), 6.65 and 6.74 (t, J=7.5 Hz, 2H each, ArH para), 6.92 and 7.06 (d, J=7.5 Hz, 4H each, ArH meta), 8.30 (s, 2H, OH).

Preparation of 2-(2-chloroethoxy)ethyl p-toluenesulfonate: Preparation was done according to a standard procedure for the preparation of p-Toluenesulfonic esters (*Organikum;* 16. Auflage (VEB Deutscher Verlag der Wissenschaften Berlin 1986) p. 559).

In a round bottom flask 9.53 g (50 mmol) of p-Toluenesulfonylchloride were mixed with 7.47 g (60 mmol) 2-(2-Chloroethoxy)ethanol in 50 ml $CHCl_3$. The mixture was stirred and cooled below 5° C. and 10.1 g (100 mmol) triethylamine were added drop-wise at this temperature. After the addition was completed, the mixture was stirred for another 3 h at room temperature. At which point, a mixture of 50 g ice and 20 ml conc. HCl was added carefully and stirred for 30 min. The chloroform phase was separated, washed three times with 30 ml water, dried with Na2SO4 and the solvent removed in vacuo upon which 12.5 g (90%) of a yellowish oil was obtained. The product was used without further purification.

Measurements of the product determined the following: $^1$H NMR ($CDCl_3$) δ2.45 (s, 3H, Ar—$CH_3$), 3.55 (t, J=7.4 Hz, 2H, $OCH_2CH_2Cl$), 3.65–3.77 (m, 4H, $OCH_2CH_2OCH_2CH_2Cl$), 4.17 (t, J=7.2 Hz, 2H, $SO_2OCH_2CH_2O$), 7.42 and 7.84 (2d, J=7.5 Hz, 2H each, ArH ortho and para), Preparation of 25,27-bis(1-propyloxy)-26,28-bis(5-chloro-3-oxapentyloxy)calix[4]arene: A solution of 2.54 g (5 mmol) 25,27-bis(1-propyloxy)calix[4]arene, 5.57 g (20 mmol) 2-(2-Chloroethoxy)ethyl p-toluenesulfonate and 3.36 g (10 mmol) $Cs_2CO_3$ in 150 ml dry acetonitrile was heated at reflux under nitrogen for 24 hr. The solvent was removed in vacuo and 50 ml 2N HCl and 50 ml $CH_2Cl_2$ were added and the phases were separated. The aqueous phase was extracted two times with 30 ml $CH_2Cl_2$, the organic phases were combined dried with Na2SO4 and the solvent removed in vacuo. The crude product was recrystallized twice from methanol/$CH_2Cl_2$ (5:1) and gave 3.07 g (85%) of 25,27-bis(1-propyloxy)-26,28-bis(5-chloro-3-oxapentyloxy)calix[4]arene as white crystals.

Measurements of the product determined the following: $^1$H NMR (CDCl$_3$) δ0.93 (t, J=7.2 Hz, 6H, OCH$_2$CH$_2$CH$_3$), δ1.65 (m, 4H, OCH$_2$CH$_2$CH$_3$), δ3.50–3.80 (m, 28H), δ6.67–6.72 (m, 4H, ArH para), δ6.97 and 7.05 (d, J=7.6 Hz, 4H each, ArH meta).

Preparation of N-tosyl 25,27-bis(1-propyloxy)calix[4]arene azacrown-5: A solution of 1.446 g (2 mmol) 25,27-bis(1-propyloxy)-26,28-bis(5-chloro-3-oxapentyloxy)calix[4]arene, 0.343 g (2 mmol) p-toluenesulfonamide and 1.38 g (10 mmol) K$_2$CO$_3$ in 70 ml dry DMF was heated at reflux under nitrogen for 24 h. The solvent was removed in vacuo and 50 ml 2N HCl and 50 ml CH$_2$Cl$_2$ were added and the phases were separated. The aqueous phase was extracted two times with 30 ml CH$_2$Cl$_2$, the organic phases were combined dried with Na2SO4 and the solvent removed in vacuo. The crude product was purified by column chromatography using ethyl acetate:hexane 1:4 (Rf=0.4) to provide 1.15 g (70%) N-Tosyl 25, 27-bis(1-propyloxy)calix[4]arene Azacrown-5. The $^1$H NMR spectrum corresponds to the published data by Kim J S et al., *J. Org. Chem.*, 65, 2386–2392 (2000).

Measurements of the product determined the following: $^1$H NMR (CDCl$_3$) δ0.72 (t, J=7.3 Hz, 6H, OCH$_2$CH$_2$CH$_3$), 1.28 (m, 4H, OCH$_2$CH$_2$CH$_3$), 2.45 (s, 3H, ArCH$_3$), 3.20–3.80 (m, 28H), 6.74–6.82 (m, 4H, ArH para), 7.01–7.06 (m, 8H, ArH meta) 7.34 (d, 2H, J=7.4 Hz TosArH ortho), 7.74 (d, 2H, J=7.4 Hz, TosArH meta).

Preparation of 25,27-bis(1-propyloxy)calix[4]arene Azacrown-5: The reductive detosylation of N-Tosyl 25,27-bis(1-propyloxy)calix[4]arene Azacrown-5 followed the procedure described by Quici S et al., *Org. Chem.*, 61, 3870–3873 (1996). Under nitrogen, 380 mg (10 mmol) LiAlH4 was added carefully to a solution of 410 mg (0.5 mmol) N-Tosyl 25,27-bis(1-propyloxy)calix[4]arene Azacrown-5 in 80 ml dry tetrahydrofuran (THF). The suspension was heated to reflux for 24 hr and then allowed to cool to room temperature (rt), and the excess LiAlH$_4$ was decomposed with stoichiometric amounts of water. The aluminum oxide was filtered off and carefully washed with 80 ml THF and the solvent evaporated. The crude product was purified on prep. TLC using ethyl acetate:hexane 1:1 (Rf=0.2) to afford 203 mg (61%) 25,27-bis(1-propyloxy)calix[4]arene Azacrown-5 as a pale yellow solid. The $^1$H NMR spectrum corresponds to the published data.

Measurements of the product determined the following: $^1$H NMR (CDCl3) δ0.82 (t, J=7.3 Hz, 6H, OCH$_2$CH$_2$CH$_3$), 1.52 (m, 4H, OCH$_2$CH$_2$CH$_3$), 2.77 (s, 4H, —OCH$_2$CH$_2$NCH$_2$—), 3.43–3.60 (m, 16H, —CH$_2$—), 3.77 (s, 8H, Ar—CH$_2$—Ar), 6.78 and 6.83 (t, J=7.5 Hz, 2H each, ArH para), 7.03 and 7.13 (d, J=7.5 Hz, 4H each, ArH meta)

Preparation of N-(9-methyl-anthracene)-25, 27-bis(1-propyloxy)calix[4]arene Azacrown-5 (2): A solution of 100 mg (0.15 mmol) 25,27-bis(1-propyloxy)calix[4]arene Azacrown-5, 35 mg (0.15 mmol) 9-(Chloromethyl) anthracene and 46 mg (0.45 mmol) triethylamine in 50 ml of dry dioxane was refluxed for 24 hr. The solvent was removed in vacuo and 50 ml 2N HCl and 50 ml CH$_2$Cl$_2$ were added and the phases were separated. The aqueous phase was extracted two times with 30 ml CH$_2$Cl$_2$, the organic phases were washed once with 30 ml of 2N NaOH, separated, dried with Na$_2$SO$_4$ and the solvent was evaporated in vacuo. The crude product was purified on prep. Thin layer chromatography (TLC) using CH$_2$Cl$_2$ (Rf=0.3) to afford 23 mg (18%) N-(9-methyl-anthracene)-25,27-bis(1-propyloxy)calix[4]arene Azacrown-5 (2) as white crystals.

Measurements of the product determined the following: $^1$H NMR (CDCl$_3$) δ0.70 (t, J=7.3 Hz, 6H, OCH$_2$CH$_2$CH$_3$), 1.21 (m, 4H, OCH$_2$CH$_2$CH$_3$), 2.70–3.85 (m, 28H), 4.57 (s, 2H, ArCH$_2$NR$_2$), 6.77–6.97 (m, 4H, ArH para), 7.01–7.08 (m, 8H, ArH meta) 7.46–8.79 (m, 9H, Anthr-ArH). $^{13}$C NMR (CDCl$_3$) δ10.42 (OCH$_2$CH$_2$(OCH$_2$CH$_2$CH$_3$), 38.57 (OCH$_2$CH$_2$CH$_3$), 54.03 (ArCH$_2$Ar), 70.167, 70.89, 71.23, 72.39, (O—CH$_2$—CH$_2$—O—CH$_2$—CH$_2$—N) 122.59, 122.69, 125.31, 125.67, 126.07, 129.42, 130.12, 130.23, 131.85, 134.18, 134.50, 157.24, 157.47.(Ar-Carbon).

Also: MS m/z (M+) calcd. 856.11 found 856.4. CH$_3$), 22.80

EXAMPLE 2

Testing of the Compound of the Invention

Testing of compound 2: Testing of the compound of the invention was performed in solution using dichloromethane at a concentration of 0.8 μM mM. Fluorescence spectra were recorded on a Perkin Elmer LS50B at an excitation wavelength of 355 nm. Alkali metals were added as the acetate salts. Alkali metals are soluble in the solvents used and have been used for other molecules in the literature.

FIG. 1 shows the fluorescence emission spectrum of compound 2 as a function of potassium concentration. As it can be seen, there is a >8 fold enhancement in the fluorescent quantum yield.

Figure 2:
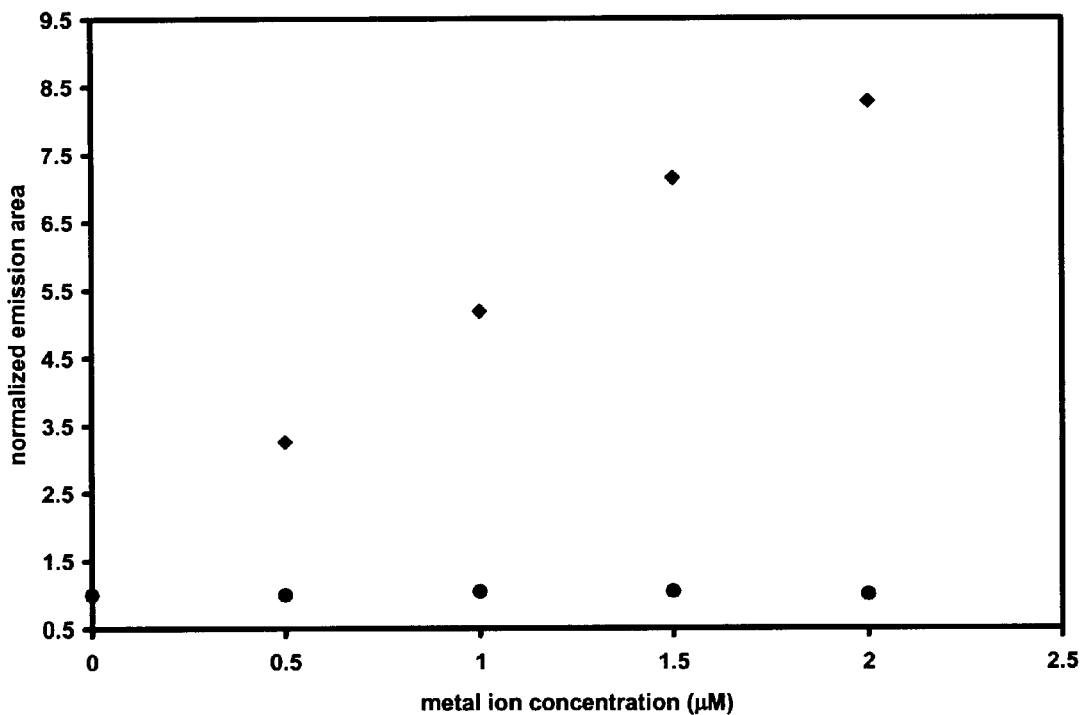
FIG. 2 shows the normalized fluorescence emission area versus the metal cation concentration of potassium and sodium.

FIG. 2 shows the normalized emission area vs. potassium and sodium concentrations. Upon addition of sodium there was no observable increase of fluorescence quantum yield showing that the novel fluorionophore discriminates against sodium to a very high degree. This is further demonstrated by an estimated selectivity coefficient (log $K_{K,Na}$) using the Fixed Interference Method (FIM) (Frant, M. S. et al. *Pure Appl. Chem.*, 48, 127 (1976)) where the log $K_{K,Na}$ is at least −3 thus indicating that the novel fluoroionophore is selective for potassium at least 1000 times more than sodium.

The data presented in FIG. 2 demonstrates that the compound of the invention is a suitable fluorophore for the selective determination of potassium.

The foregoing description has been presented only for the purposes of illustration and is not intended to limit the invention to the precise form disclosed, but by the claims appended hereto.

We claim:

1. A compound, having the structure:

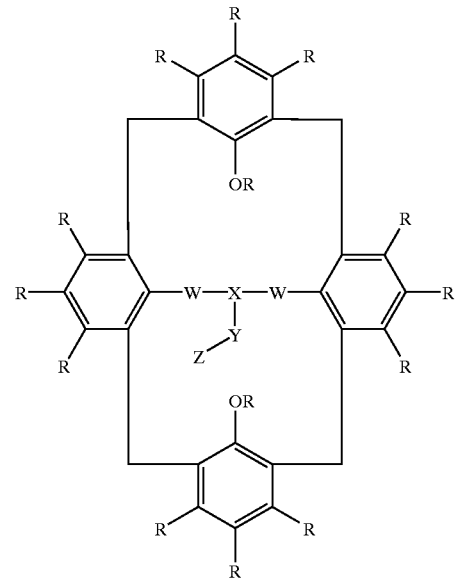

wherein
(a) R is selected from the group consisting, independently or in combination, of hydrogen, alkyl, alkenyl, alkynyl, alkoxy, ether, acyl, carboxylic acid, carboxylic ester, unsubstituted aryl substituted aryl, aryloxy, heteroaryl, and heteroaryloxy groups, wherein the heteroatom is selected from nitrogen and sulfur;
(b) W is —O(CH$_2$)$_2$O(CH$_2$)$_2$—;
(c) X is selected from the group consisting, independently or in combination, of nitrogen, saturated alkyl, unsaturated alkyl, unsubstituted aryl, and substituted aryl, wherein the aryl group may contain a heteroatom selected from the group consisting of nitrogen, sulfur and oxygen;

(d) Y is selected from the group consisting, independently or in combination, of saturated alkyl, unsaturated alkyl, unsubstituted aryl, substituted aryl, ether, carboxylic acid, carboxylic ester, secondary amine and sulfur; and (e) Z is a fluorophore, wherein a negative, thermo-neutral or slightly positive free energy value is obtained from the Rehm-Weller equation for the compound.

2. The compound of claim 1, wherein the compound is a calix[4]arene derivative.

3. The compound of claim 1, wherein the fluorophore is anthracene.

4. The compound of claim 1, having the structure:

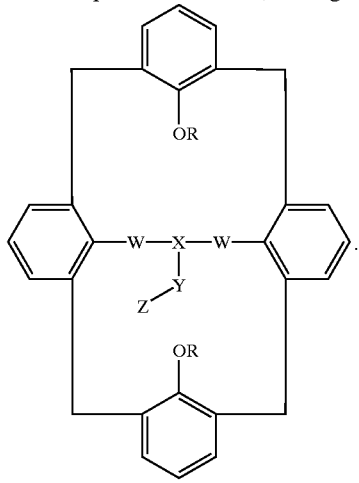

5. The compound of claim 4, wherein R is a propyl group.
6. The compound of claim 4, wherein W is —O(CH$_2$)$_2$O(CH$_2$)$_2$—.
7. The compound of claim 4, wherein X is nitrogen.
8. The compound of claim 4, wherein Y is —CH$_2$—.
9. The compound of claim 4, wherein Z is anthracene.
10. The compound of claim 1, further comprising a transparent matrix material in which the compound of claim 1 is situated.
11. The compound of claim 7, wherein the matrix material is a transparent glass or a transparent polymer.
12. A method for measuring potassium ion concentration in a fluid sample, comprising the steps of:
(a) obtaining an optode comprising the fluoroionophore having the structure:

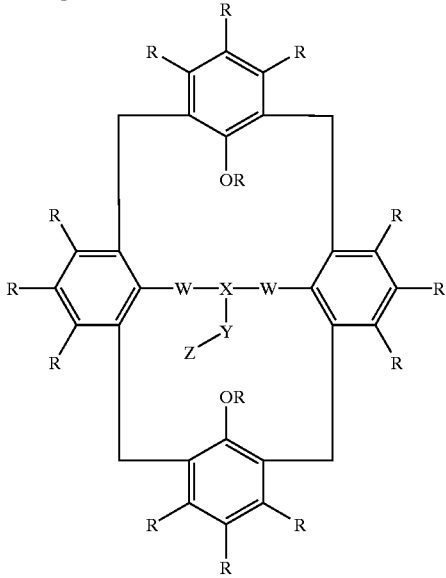

wherein
(i) R is selected from the group consisting, independently or in combination, of hydrogen, alkyl, alkenyl, alkynyl, alkoxy, ether, acyl, carboxylic acid, carboxylic ester, unsubstituted aryl substituted aryl, aryloxy, heteroaryl, and heteroaryloxy groups, wherein the heteroatom is selected from nitrogen and sulfur;
(ii) W is —O(CH$_2$)$_2$O(CH$_2$)$_2$—;
(iii) X is selected from the group consisting, independently or in combination, of nitrogen, saturated alkyl, unsaturated alkyl, unsubstituted aryl, and substituted aryl, wherein the aryl group may contain a heteroatom selected from the group consisting of nitrogen, sulfur and oxygen;
(iv) Y is selected from the group consisting, independently or in combination, of saturated alkyl, unsaturated alkyl, unsubstituted aryl, substituted aryl, ether, carboxylic acid, carboxylic ester, secondary amine and sulfur; and
(v) Z is a fluorophore, wherein a negative, thermoneutral or slightly positive free energy value is obtained from the Rehm-Weller equation for the compound;

(b) contacting the optode with a fluid sample suspected of containing potassium ions; and
(c) measuring the fluorescence from the optode following the contacting of the optode with the fluid sample, wherein the fluorescence from the optode can be correlated with the activity of the potassium ions in the fluid sample.

13. The method of claim 12, wherein the measuring is by spectrofluorimetry.

14. A method for measuring potassium ion concentration in a cell of an organism, comprising the steps of:
(a) introducing into the cell a fluoroionophore having the structure:

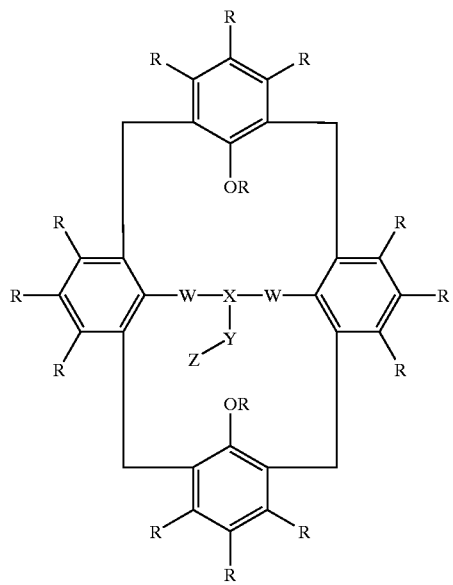

wherein
(i) R is selected from the group consisting, independently or in combination, of hydrogen, alkyl, alkenyl, alkynyl, alkoxy, ether, acyl, carboxylic acid, carboxylic ester, unsubstituted aryl substituted aryl, aryloxy, heteroaryl, and heteroaryloxy groups, wherein the heteroatom is selected from nitrogen and sulfur;

(ii) W is —O(CH$_2$)$_2$O(CH$_2$)$_2$—;
(iii) X is selected from the group consisting, independently or in combination, of nitrogen, saturated alkyl, unsaturated alkyl, unsubstituted aryl, and substituted aryl, wherein the aryl group may contain a heteroatom selected from the group consisting of nitrogen, sulfur and oxygen;
(iv) Y is selected from the group consisting, independently or in combination, of saturated alkyl, unsaturated alkyl, unsubstituted aryl, substituted aryl, ether, carboxylic acid, carboxylic ester, secondary amine and sulfur; and
(v) Z is a fluorophore, wherein a negative, thermo-neutral or slightly positive free energy value is obtained from the Rehm-Weller equation for the compound; and (b) measuring the fluorescence from the cell following the introduction of the fluoroionophore into the cell, wherein the fluorescence from the cell can be correlated with the activity of the potassium ions in the cell.

15. A method for measuring potassium ion activity in a fluid sample, comprising the steps of:
(a) introducing into the fluid sample a fluoroionophore having the structure:

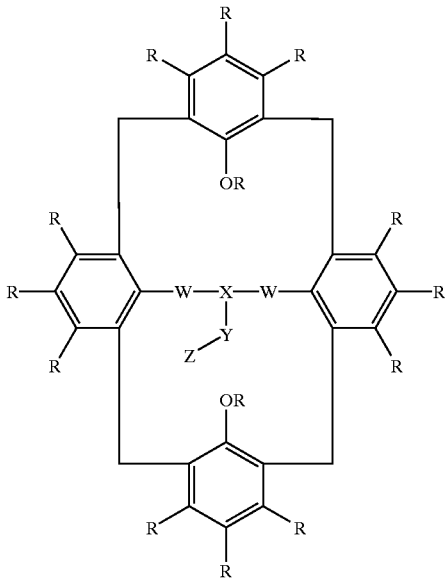

wherein
(i) R is selected from the group consisting, independently or in combination, of hydrogen, alkyl, alkenyl, alkynyl, alkoxy, ether, acyl, carboxylic acid, carboxylic ester, unsubstituted aryl substituted aryl, aryloxy, heteroaryl, and heteroaryloxy groups, wherein the heteroatom is selected from nitrogen and sulfur;
(ii) W is —O(CH$_2$)$_2$O(CH$_2$)$_2$—;
(iii) X is selected from the group consisting, independently or in combination, of nitrogen, saturated alkyl, unsaturated alkyl, unsubstituted aryl, and substituted aryl, wherein the aryl group may contain a heteroatom selected from the group consisting of nitrogen, sulfur and oxygen;
(iv) Y is selected from the group consisting, independently or in combination, of saturated alkyl, unsaturated alkyl, unsubstituted aryl, substituted aryl, ether, carboxylic acid, carboxylic ester, secondary amine and sulfur; and
(v) Z is a fluorophore, wherein a negative, thermo-neutral or slightly positive free energy value is obtained from the Rehm-Weller equation for the compound; and (b) measuring the fluorescence from the cell following the introduction of the fluoroionophore into the cell, wherein the fluorescence from the cell can be correlated with the activity of the potassium ions in the cell.

16. A sensor, consisting essentially of a carrier and an active layer applied to the carrier, wherein the active layer comprises a transparent support material in which a compound is situated, the compound having the structure:

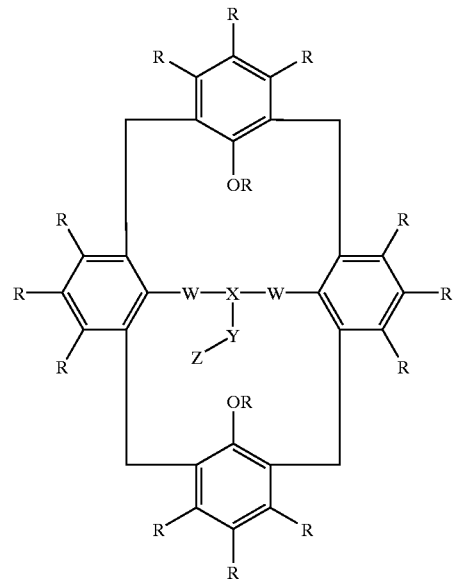

wherein
(a) R is selected from the group consisting, independently or in combination, of hydrogen, alkyl, alkenyl, alkynyl, alkoxy, ether, acyl, carboxylic acid, carboxylic ester, unsubstituted aryl, substituted aryl, aryloxy, heteroaryl, and heteroaryloxy groups, wherein an aryl group may contain a heteroatom selected from the group consisting of nitrogen and sulfur;
(b) W is —O(CH$_2$)$_2$O(CH$_2$)$_2$—;
(c) X is selected from the group consisting, independently or in combination, of nitrogen, saturated alkyl, unsaturated alkyl, unsubstituted aryl, and substituted aryl, wherein an aryl group may contain a heteroatom selected from the group consisting of nitrogen, sulfur and oxygen;
(d) Y is selected from the group consisting, independently or in combination, of saturated alkyl, unsaturated alkyl, unsubstituted aryl, substituted aryl, ether, carboxylic acid, carboxylic ester, secondary amine and sulfur; and
(e) Z is a fluorophore, wherein a negative, thermo-neutral or slightly positive free energy value is obtained from the Rehm-Weller equation for the compound.

17. The sensor of claim 16, wherein the compound is a calix[4]arene derivative.

18. The sensor of claim 16, wherein the fluorophore is anthracene.

19. The sensor of claim 16, wherein the compound has the structure:

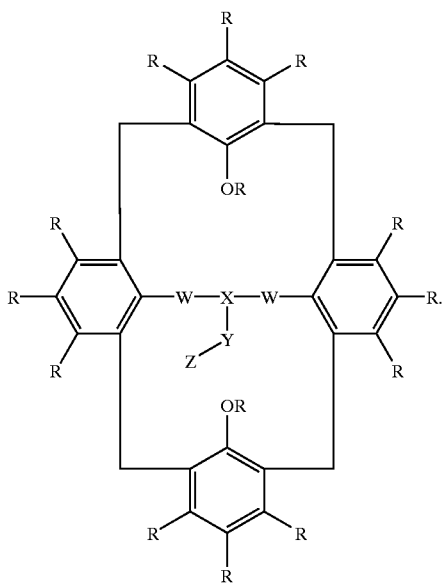

20. The sensor of claim 19, wherein R is a propyl group.
21. The sensor of claim 19, wherein W is —O(CH$_2$)$_2$O(CH$_2$)$_2$—.
22. The sensor of claim 19, wherein X is nitrogen.
23. The sensor of claim 19, wherein Y is —CH$_2$—.
24. The sensor of claim 19, wherein Z is anthracene.
25. The sensor of claim 16, wherein the support material is transparent glass, transparent polymer, transparent co-polymer or polymeric mixture.
26. The sensor of claim 16, wherein the support material is selected from the group consisting of plasticized or non plasticized poly(vinyl chloride) (PVC), sol-gel materials, polyvinylformal-silica mixtures, hydrogels, polyurethanes, and mixtures thereof.
27. The sensor of claim 16, wherein the carrier is an organic or inorganic glass.
28. The sensor of claim 16, wherein the carrier is an optic fiber bundle.

* * * * *